(12) United States Patent
Peng et al.

(10) Patent No.: US 6,287,250 B1
(45) Date of Patent: Sep. 11, 2001

(54) METHOD AND APPARATUS FOR CARDIAC LIFTING DURING BEATING HEART SURGERY USING PERICARDIAL CLIPS

(75) Inventors: Steven Peng, Menlo Park; Grace A. Carlson, San Francisco; Albert K. Chin, Palo Alto, all of CA (US)

(73) Assignee: Origin Medsystems, Inc., Menlo Park, CA (US)

( * ) Notice: Subject to any disclaimer, the term of this patent is extended or adjusted under 35 U.S.C. 154(b) by 0 days.

(21) Appl. No.: 09/400,326

(22) Filed: Sep. 21, 1999

(51) Int. Cl.$^7$ .............................. A61B 19/00; A61B 17/01
(52) U.S. Cl. ............................................... 600/37; 600/218
(58) Field of Search ............................. 600/37, 205, 204, 600/214, 218, 226, 219, 235, 206, 229; 128/898

(56) References Cited

U.S. PATENT DOCUMENTS

| D. 293,470 | 12/1987 | Adler . |
| 2,082,782 | 6/1937 | Allen . |
| 3,584,822 | 6/1971 | Oram . |
| 4,217,890 | 8/1980 | Owens . |
| 4,457,300 | 7/1984 | Budde . |
| 4,637,377 | 1/1987 | Loop . |
| 4,827,926 | 5/1989 | Carol . |
| 4,852,552 | 8/1989 | Chaux . |
| 4,949,927 | 8/1990 | Madocks et al. . |
| 4,957,477 | 9/1990 | Lundback . |
| 5,131,905 | 7/1992 | Grooters . |
| 5,139,517 | 8/1992 | Corral . |
| 5,150,706 | 9/1992 | Cox et al. . |
| 5,256,132 | 10/1993 | Snyders . |
| 5,348,259 | 9/1994 | Blanco et al. . |
| 5,453,078 | 9/1995 | Valentine et al. . |
| 5,480,425 | 1/1996 | Ogilive . |
| 5,509,890 | 4/1996 | Kazama . |
| 5,632,746 | 5/1997 | Middleman et al. . |
| 5,662,300 | 9/1997 | Michelson . |
| 5,683,349 | * 11/1997 | Makower et al. ............ 600/214 |
| 5,727,569 | 3/1998 | Benetti et al. . |
| 5,730,757 | 3/1998 | Benetti et al. . |
| 5,782,746 | 7/1998 | Wright . |
| 5,799,661 | 9/1998 | Boyd et al. . |
| 5,807,243 | 9/1998 | Vierra et al. . |
| 5,836,311 | 11/1998 | Borst et al. . |
| 5,865,730 | 2/1999 | Fox et al. . |
| 5,875,782 | * 3/1999 | Ferrari et al. ............ 128/898 |
| 5,899,425 | 4/1999 | Corey, Jr. et al. . |
| 5,899,853 | * 5/1999 | Fowler, Jr. ............ 600/217 |
| 5,906,607 | 5/1999 | Taylor et al. . |
| 5,927,284 | 7/1999 | Borst et al. . |
| 6,019,722 | * 2/2000 | Spence et al. ............ 600/210 |
| 6,036,641 | * 3/2000 | Taylor et al. ............ 600/231 |

FOREIGN PATENT DOCUMENTS

| 0 820 721 A1 | 7/1997 | (EP) ............... A61B/17/02 |
| 0 791 330 A2 | 8/1997 | (EP) . |
| 0 808 606 A1 | 11/1997 | (EP) ............... A61B/17/02 |
| WO 96/40354 | 12/1996 | (WO) ............... A61M/37/100 |
| WO 97/10753 | 3/1997 | (WO) . |
| WO 97/40738 | 11/1997 | (WO) . |
| WO 98/37814 | 9/1998 | (WO) . |

OTHER PUBLICATIONS

Angelini, G. D., "A Simple, Inexpensive Method of Heart Retraction During Coronary Artery Bypass Surgery," Ann Thorac Surg, 46:246–247, Dec. 1998.

(List continued on next page.)

Primary Examiner—Samuel G. Gilbert
(74) Attorney, Agent, or Firm—Alan W. Cannon; Bozicevic, Field & Francis LLP (57) ABSTRACT

A clip which can be temporarily clamped to a cut edge of a pericardium during heart surgery. Two or more of the clips, which may be each connected to a respective flexible member, are clipped to the pericardium and tension is applied to the connectors to suspend the clips and the pericardium, as well as the heart, form a support, while enabling the heart to continue to beat normally.

27 Claims, 4 Drawing Sheets

OTHER PUBLICATIONS

Borst, et al., "Coronary Artery Bypass Grafting Without Cardiopulmonary Bypass and Without Interruption of Native Coronary Flow Using a Novel Anastomosis Site Restraining Device ('Octopus')," JAAC vol. 27, No. 6, May 1996: 1356–64.

Calvin, I. F. & Newman, D.C., "Circumflex Exposure Using a Cardiac Sting," Ann Thorac Surg Dec. 1990:49:833–4.

Grundeman et al., "Vertical Displacement of the Beating Heart by the Octupus Tissue Stabilizer: Influence on Coronary Flow," Ann Thorac Surg Dec. 1998:65–1348–52.

Grundeman et al., "Hemodynamic Changes During Displacement of the Beating Heart by the Utrecht Octopus Method," Ann Thorac Surg Dec. 1997:63:S88–92.

Janke, W. H., "Heart Support for Coronary Bypass Surgery Involving the Circumflex Artery System," The Journal of Thoracic and Cardiovascular Surgery, pp. 883–884, Dec. 1974.

Jansen et al., "Off–Pump Coronary Bypass Grafting: How to Use the Octopus Tissue Stabilizer," Ann Thorac Surg, Dec. 1998;66:576–9.

Jansen et al., "Experimental Off–Pump Grafting of a Circumflex Branch Via Sternotomy Using a Suction Device," Ann Thorac Surg, Dec. 199;63:S93–6.

Kazama, Shigeru & Ishihara, Akira, "Fabric Heart Retractor for Coronary Artery Bypass Operations," Ann Thorac Surg, Dec. 1993; 55:1582–3.

Matsura et al., "A New Device fo Exposing the Circumflex Coronary Artery," Ann Thorac Surg, 1995; 59:1249–50.

Rousou et al., "Cardiac Retractor for Coronary Bypass Operations," Ann Thorac Surg., Dec. 1991;52:877–8.

Splittgerber et al., "Exposing the Circumflex Coronary Artery: The Heartflip Technique,"Ann Thorac Surg. Dec. 1996;61:1019–20.

Takahashi et al., "A New Instrument for Immobilization and Hemostasis During Minimally Invasive Direct Coronary Artery Bypass ('MIDCAB doughnut'): Experimental Study," J Cardio Surg, Dec. 1997;12:185–189.

* cited by examiner

METHOD AND APPARATUS FOR CARDIAC LIFTING DURING BEATING HEART SURGERY USING PERICARDIAL CLIPS

FIELD OF THE INVENTION

The invention pertains to an apparatus for elevating or otherwise manipulating an organ such as a beating heart (and supporting the organ in a retracted position). Preferred embodiments of the invention pertain to an apparatus for supporting and manipulating a beating heart during surgery thereon.

BACKGROUND OF THE INVENTION

Coronary artery bypass grafting (CABG) has traditionally been performed with the use of a cardiopulmonary bypass (CPB) machine to oxygenate and perfuse the body during surgery. Recently, techniques have been developed to allow for performing CABG without the use of CPB by stabilizing the epicardial surface of a beating heart at the coronary anastomotic site with a stabilizer (e.g., stabilizing feet) to allow placement of sutures through the graft vessel and recipient coronary artery. This procedure may be performed through a partial or full sternotomy, or via a thoracotomy (which is an incision between two adjacent ribs).

Access to the left anterior descending (LAD) coronary artery is easily performed by either a sternotomy or a thoracotomy. However, the patient typically requires bypass to multiple coronary arteries, including the circumflex artery (CxA) on the left lateral aspect of the heart, the right coronary artery (RCA) on the right lateral aspect of the heart, and the posterior descending artery (PDA) on the back side of the heart. It is very difficult to access the CxA, RCA, and PDA without a sternotomy, as the heart needs to be turned or tilted (or turned and tilted) significantly to reach its side or back, and with an intact sternum, insufficient space exists for these maneuvers. For example, the apex of the heart is generally lifted out of the body through a sternotomy in order to reach the PDA. Surgeons often place the patient in a Trendelenberg position, with the operating table tilted so that the patient's head lies lower than the feet with the patient in supine position, in order to assist with lifting the heart up and back.

An additional challenge to beating heart surgery is that some hearts do not tolerate manipulation well from a hemodynamic standpoint. The potential exists with current manipulation techniques to compress the heart (e.g., by pressing it with stabilization feet) or great vessels (aorta or vena cava) in such a way that hemodynamic function is compromised.

There is a need for a beating heart retraction apparatus capable of physically translating a beating heart from its natural resting place to a location better suited to surgical access, and then holding the beating heart in the latter location during surgery without compressing (or otherwise deforming) the heart or great vessels in such a way that hemodynamic function is compromised.

Figure 1:
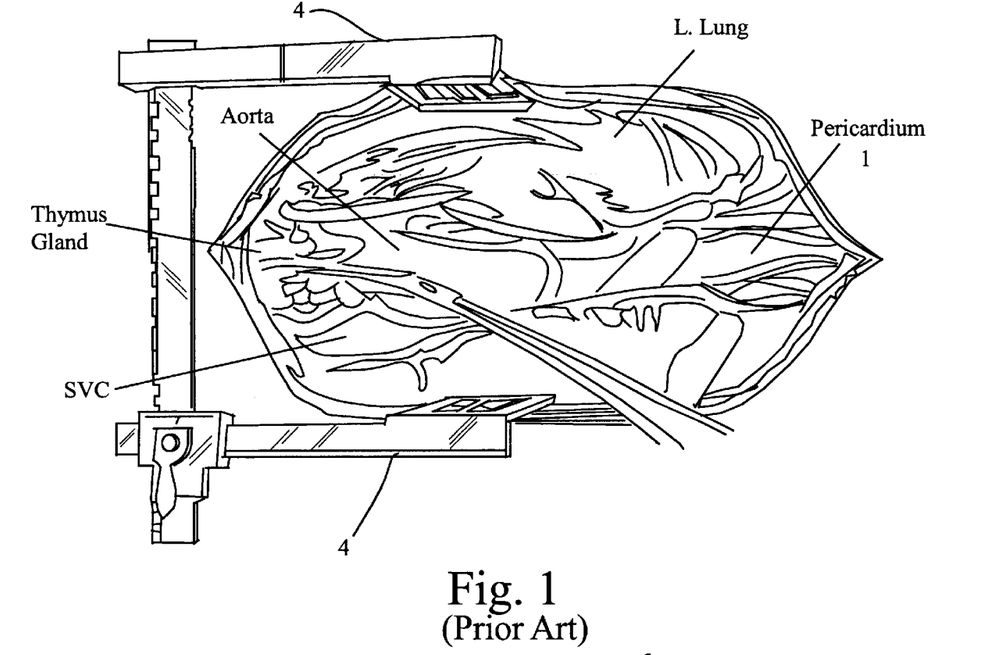
FIG. 1 is a perspective view of a conventional sternal retractor positioned to hold open a sternotomy incision, thus exposing the pericardium of a heart.
Figure 2:
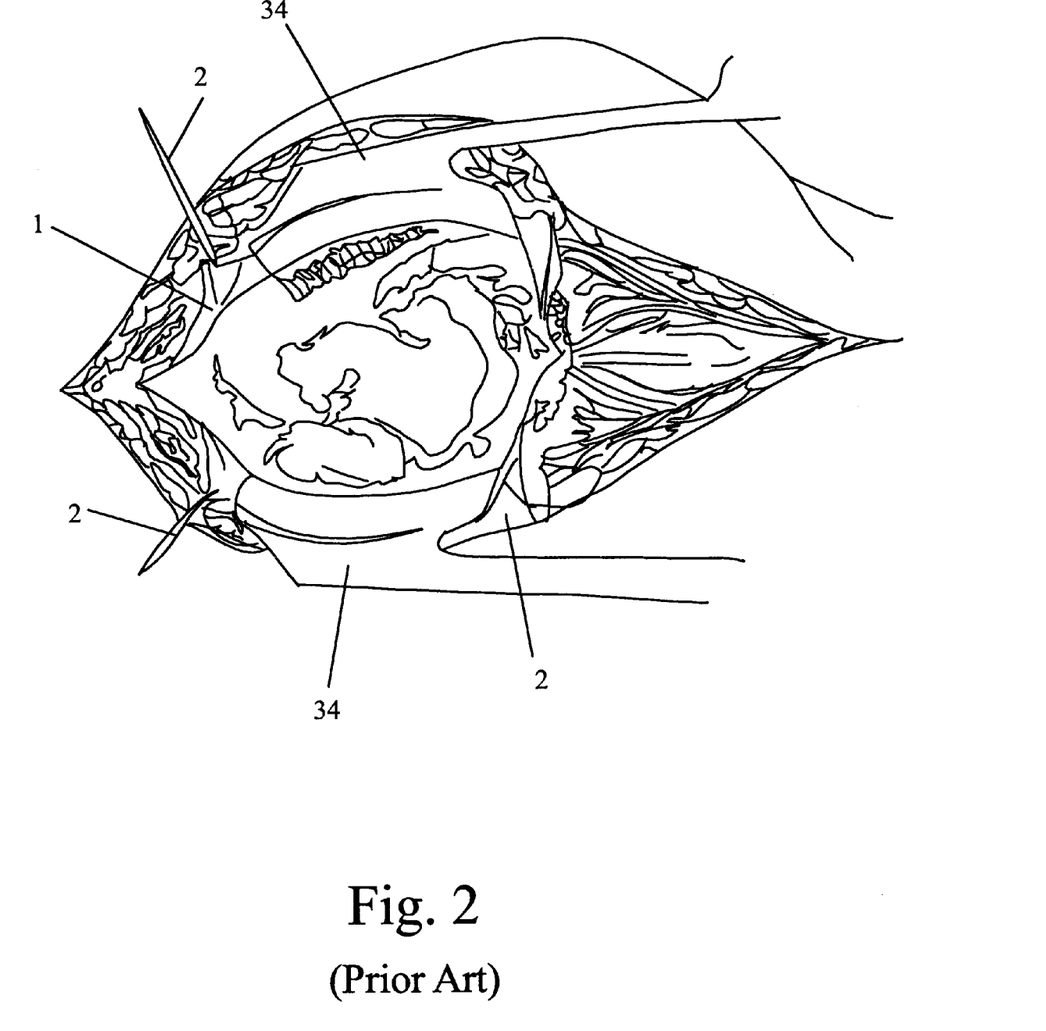
FIG. 2 is a perspective view of conventional sutures which have been placed in an incised pericardium of a heart (with a sternal retractor positioned to hold open the sternotomy incision). The sutures are tensioned to retract the heart (by lifting it) into a position for surgery.

Typically, beating heart surgery may be accomplished through a partial or full sternotomy using pericardial sutures to retract the heart (outward toward the open sternotomy) into the proper position for surgery, and using a stabilization apparatus (e.g., stabilizing feet) to stabilize the portion of the heart surface to be cut. Sometimes, surgery is performed on the properly positioned heart without using a stabilization apparatus. Before the heart is retracted, a sternal retractor (e.g., sternal retractor 4 of FIG. 1 or sternal retractor 34 of FIG. 2) is positioned to hold the sternotomy incision open, pericardium 1 is then incised along its anterior aspect, and sutures 2 are then placed in the cut edges of the pericardium (as shown in FIG. 2). In FIG. 2, sternal retractor 34 (which is a variation on sternal retractor 4 of FIG. 1) holds the sternotomy incision open. Sutures 2 are then tensioned to expose the heart and to cause the pericardium to lift the heart (as also shown in FIG. 2), thereby retracting the heart. For increased lift (e.g., to attain sufficient lift to access the posterior aspect of the heart), the sutures are often placed deep in the posterior portion of the pericardium.

A disadvantage of piercing through the pericardium in its posterior aspect (with a needle) to place deep sutures is that the pleura (identified by reference numeral 21 in FIG. 3 to be discussed below) is typically also pierced by the needle. The pleura houses the lungs on each side of the mediastinum (which contains the heart) and lies in apposition to the pericardium. Anteriorly, the pericardial surface is free; laterally, it lies against the pleura. When the pleura is punctured, air enters into the pleural cavity and the lungs collapse. At the end of the bypass procedure, bilateral chest tubes must be placed in the chest, and suction used for one or more days to maintain the lungs in an inflated condition. The chest tubes are uncomfortable, painful to remove, and restrict patient ambulation, which is important to early postsurgical recovery.

Conventional use of pericardial sutures for retraction of a beating heart has other limitations and disadvantages including the following. It is inconvenient and potentially harmful to the patient to incise the pericardium and insert sutures along cut edges of the pericardium, and then exert tension on the sutures to move the heart together as a unit with the pericardium. When the sutures are pulled to lift the heart (with pericardium), compressive force exerted by the pericardium on at least one side of the heart sometimes constrains cardiac contraction and expansion.

There are three distinct stages involved in preparing an artery (on an organ) for anastomosis:

1. gross manipulation: the organ is physically translated from its natural resting place to a location better suited to surgical access;
2. artery presentation: the target artery on the organ is identified and the position of the organ is finely adjusted so that the target artery is approachable; and
3. artery stabilization: the target artery and surrounding tissues are immobilized, allowing fine surgical techniques on very small features.

The present invention pertains to an improved method and apparatus for retraction (gross movement) of a beating heart into a desired position and orientation to allow surgery to be performed on the heart, without the limitations and disadvantages of conventional use of pericardial sutures to retract a heart for surgery.

SUMMARY OF THE INVENTION

In a class of embodiments, the invention is a clip which can be temporarily clamped to a cut edge of the pericardium at the lateral border of a heart during surgery, or a set of such clips. In use during heart surgery, two or more of the clips (each attached to a length of flexible tubing or suture material, or to another flexible connector) are clamped to the pericardium and tension is applied to the connectors to suspend the clips and pericardium from a support. The clips can be placed through a sternotomy incision (in which case the support can be a sternal retractor which holds open the incision), a thoracotomy incision, or another opening (or openings) made to expose the pericardium.

Suspension of the pericardium using the clips gives the same ability to retract the heart as does conventional suspension of the pericardium using sutures placed (using a needle) in the posterior portion of the pericardium, but without puncturing the pleura (as typically occurs when sutures are so placed in the pericardium).

Preferably, each clip comprises a pair of relatively long jaws (which pivot about a pivot point), and a ratchet lock close to the pivot point of the clip for releasably locking the jaws in a position in which they clamp the edge of a pericardium. A flexible connector (e.g., of suture material or vinyl tubing) is attached to the clip close to its pivot point. When the clip is closed and locked on the pericardium and the connector is tensioned, the pericardium lifts the heart out of the chest toward the sternotomy incision. The long jaws of the clip allow the clip to reach posteriorly, for greater heart lift. The portion of the clip proximal to the pivot is kept short, so that it does not protrude significantly above the height of the chest as the pericardium is tensioned. A low proximal clip profile is important in avoiding intrusion.

The clips hold the pericardium with sufficient force to allow retraction of the heart together as a unit with the pericardium (as the clips lift the pericardium), and to maintain the heart in the desired position during surgery.

More specifically, in preferred embodiments of the inventive method: the pericardium is freed from the adjacent pleura; at least two locking clips are then placed on the inferior incised edge of the pericardium near the apex of the heart, and the clips are advanced as deep as the jaw length will allow to grasp the pericardium as posteriorly as possible; the clips are then locked; and connectors (e.g., of suture or flexible tubing) attached to the clips are then tensioned (thereby lifting the pericardium and heart into a retracted position for surgery) and fixed onto a support (which is a sternal retractor, in some embodiments) to maintain the heart in the retracted position during a surgical procedure. After the surgical procedure, the clips are unlocked to release the pericardium.

The inventive method is useful to facilitate beating heart surgery, since the heart is free to beat while it is lifted by the clamped pericardium and maintained in the retracted position. The retracted heart is free to expand and contract normally (or nearly normally) so that hemodynamic function is not significantly compromised. In addition, the pleura is not compromised by suturing into the deep pericardium as occurs with prior (known) techniques.

Figure 5:
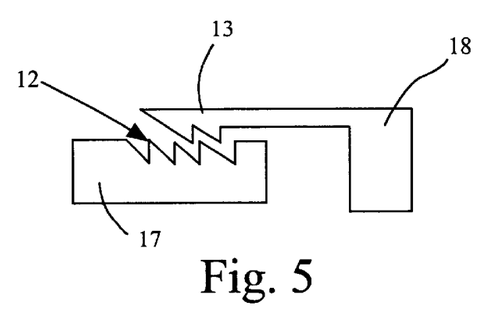
FIG. 5 is a cross-sectional view of a preferred implementation of the ratchet lock portion of the clip of FIG. 4.

In preferred embodiments, tined guides (each having a set of tines) are attached to the arms of a sternal retractor, and the connectors are secured in grooves between adjacent tines of the guides (as shown in FIG. 5).

DETAILED DESCRIPTION OF THE PREFERRED EMBODIMENTS

Throughout this disclosure, including in the claims, the expression "flexible connector" is used in a broad sense to denote any flexible mechanical coupling (for attachment to one of the inventive clips) which is made of material suitable for PATENT surgical applications and is capable of bearing (with each other clip and connector being used to lift the pericardium and heart) the combined load of the clip and a pericardium and heart suspended from the clip. Any of a wide variety of elements can be used to implement the connector, including (but not limited to) a length of flexible plastic, synthetic rubber, or silicone tubing or suture material. The expression "elastic connector" is used to denote an elastic "flexible connector."

Figure 3:
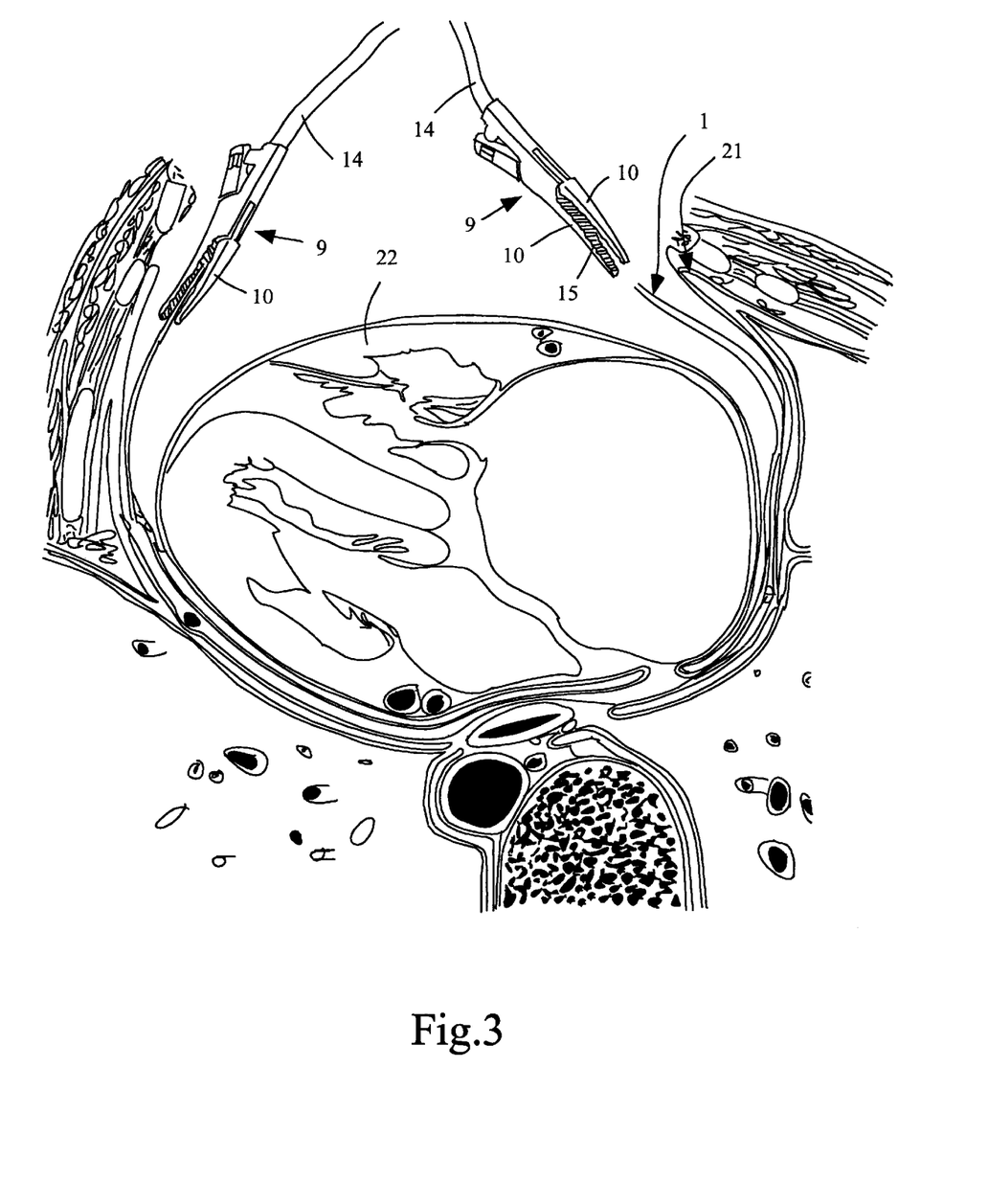
FIG. 3 is a perspective view of a preferred embodiment of a pair of the inventive locking clips, with a cross-sectional view of a pericardium (to which the clips are intended to attach) and adjacent tissue and organs.

A first preferred embodiment of the invention will be described with reference to FIGS. 3 and 4. FIG. 3 is a transverse section through a human patient at the level of the heart, with a sternotomy having been performed on the patient to sever and separate the sternum, pleura (21), and pericardium (1) as shown. FIG. 3 shows two clips 9 (each embodying the present invention) being applied to the cut edges of the pericardium (with the pericardium having been separated from the adjacent pleura). The jaws 10 of each clip 9 have gripping surfaces 15 designed for engagement with pericardium 1. Each clip 9 is attached to a flexible connector 14. Flexible connector 14 is preferably an elastic connector (e.g., a length of rubber or elastomeric tubing) but is alternatively a flexible connector that is inelastic (or has low elasticity), such as a length of flexible vinyl tubing or suture material. Jaws 10 are advanced into engagement with pericardium 1 and then locked together in a configuration in which each clip 9 is releasably clamped to the pericardium. Connectors 14 are then tensioned to lift pericardium 1 toward the top of FIG. 3, thus retracting heart 22 from the chest cavity (with the heart supported by the pericardium as by a sling). Suspension of the pericardium using clips 9 is functionally equivalent to placement of sutures in the posterior portion of the pericardium, without need to puncture the pleura.

Figure 4:
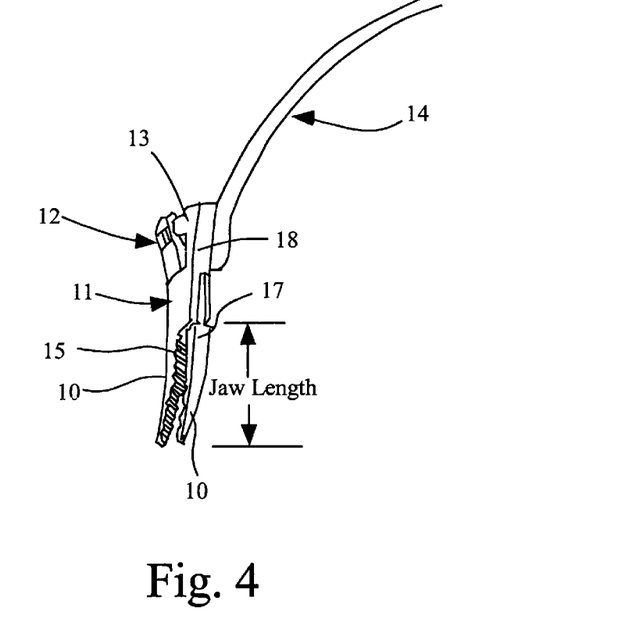
FIG. 4 is a perspective view of a preferred embodiment of the inventive locking clip.

FIG. 4 is a perspective view of a preferred embodiment of one of the locking clips 9 of FIG. 3. Clip 9 comprises two elements (17 and 18) pivotably connected together at pivot point 11. Each of elements 17 and 18 has a distal end (at the bottom of FIG. 4) which defines a relatively long jaw 10. The proximal ends of elements 17 and 18 (opposite the distal ends) define a ratchet lock, with the ratchet lock preferably being closer to pivot point 11 than are the distal ends of jaws 10. The ratchet lock comprises sawtooth rack 12 (defined by pivoting element 17) and sawtooth rack 13 (defined by pivoting element 18) which can be locked against any of several subsets of the teeth of rack 12. FIG. 5 shows an implementation of racks 12 and 13. To lock jaws 10 together, teeth of rack 13 are engaged with teeth of rack 12 (i.e., so that the elements 17 and 18 are prevented from moving away from each other by the shape of the engaged teeth). By squeezing together the proximal ends of the pivoting elements with flange 13 engaged with rack 12 and a pericardium or other object positioned between jaws 10, jaws 10 are successively locked into positions with successively reduced inter-jaw separation (i.e., as rack 13 moves toward the left of FIG. 5 relative to rack 12). Specifically, the force of teeth of rack 12 (which are engaged with teeth of rack 13) on rack 13 prevents the jaws 10 from separating, and the force exerted in the opposite rotational direction on element 18 (and thus on rack 13) by the object clamped between jaws 10 prevents the jaws from moving closer to each other. To unlock jaws 10 (so they are free to move apart from each other), pivoting elements 17 and 18 of clip 9 are flexed so that the rack 13 disengages from rack 12 (i.e., rack 13 is flexed out of the plane of FIG. 5 relative to rack 12). Alternative locking mechanisms such as spring loaded, snap fit, or latch over lock mechanisms are within the scope of the invention.

Each jaw 10 has a gripping surface 15 designed to engage and grip the pericardium. Preferably, each gripping surface 15 is grooved (as shown) or otherwise has a rough texture. Alternatively, a gripping surface of each jaw is provided by coating or covering an appropriate portion of the jaw with rubber, silicone, fabric, or other material that provides sufficient traction on the pericardium to accomplish the intended use of the clip. In typical implementations of such alternative embodiments, the clip is made of smooth metal or other smooth material suitable for surgical applications, and all or part of each jaw thereof is coated or covered by rubber, silicone, or fabric that defines a gripping surface providing sufficient traction to accomplish the intended use of the clip.

Flexible tubing 14 (which is preferably made from vinyl) is attached to clip 9 at a location near to pivot point 11. In alternative embodiments, each length of tubing 14 is replaced by a length of suture material or another flexible connector.

When jaws 10 of each of two or more clips 9 are closed on the pericardium (and locked together with fixed inter-jaw spacing), the lengths of tubing 14 are tensioned so that clips 9 pull the pericardium (thereby lifting the heart out of the chest (toward the sternotomy incision). Due to their long length, jaws 10 allow each clip 9 to reach posteriorly (to achieve greater heart lift). The portion of each clip 9 proximal to pivot point 11 is kept short, so it does not protrude significantly above the height of the chest when the flexible connector is tensioned (to retract the heart). A low profile for the proximal portion of each clip is important to avoid intrusion into the surgeon's working space.

Following performance of a sternotomy, the pericardium is freed from the adjacent pleura. Preferably, two of the inventive clips are placed on the inferior incised edges of the pericardium, near the apex of the heart so that the pericardium (and heart) can be lifted into a desired retracted position for heart surgery. More generally, at least two of the clips are positioned at appropriate points along the incised edges of the pericardium so that the pericardium (and heart) can be lifted into a desired retracted position for heart surgery. The clips are advanced as deep as the jaw length will allow, to grasp the pericardium as posteriorly as possible, and the jaws of each clip are then locked to each other. The flexible connector attached to each clip is tensioned (to lift the pericardium and heart) and fixed onto a rigid structure (preferably a sternal retractor).

Figure 6:
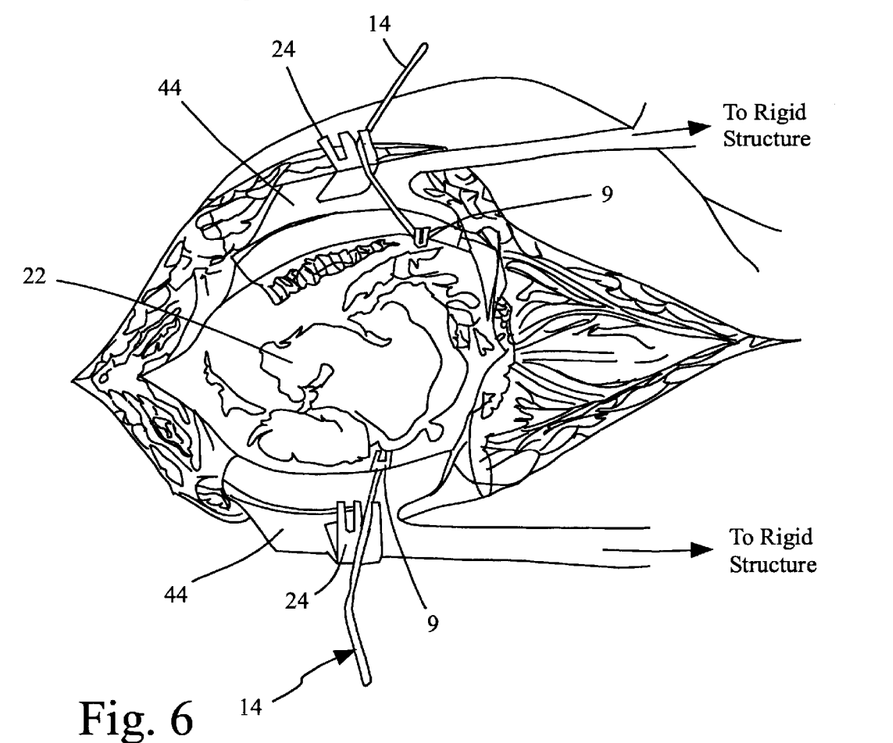
FIG. 6 is a perspective view of a preferred embodiment of the invention, including locking clips mounted to flexible tubing, and tined guides for holding the tubing in desired positions.
Figure 7:
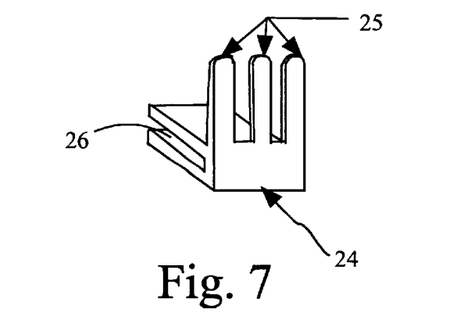
FIG. 7 is a perspective view of one of the tined guides of FIG. 6.

One embodiment of hardware for fixing the clip connectors to a sternal retractor will be described with reference to FIGS. 6 and 7. The sternal retractor of FIG. 6 comprises two arms 44 which are locked into a rigid configuration to hold open a sternotomy incision thus exposing heart 22. Two of the inventive clips 9 locked onto the incised pericardium near the apex of the heart (as shown) and flexible connectors 14 (preferably consisting of lengths of flexible vinyl tubing or other flexible tubing) attached to clips 9 are tensioned to retract the heart. A tined guide 22 is fixedly attached to each arm 44 of the sternal retractor. To fix the tensioned connectors 14 to the sternal retractor, each connector 14 is squeezed between two tines 25 of one of the guides 24 (or is tied or otherwise secured to one of the guides 24).

A preferred embodiment of each guide 24 will be described with reference to FIG. 7. As shown in FIG. 7, this embodiment of guide 24 is made of rigid material, and comprises three parallel tines 25. Each pair of adjacent tines 25 is separated by a groove dimensioned for securing one of connector 14. Guide 24 has a slot 26 for receiving an edge of a sternal retractor arm 44, so that each guide 24 can be secured to the sternal retractor.

In other embodiments of the invention, an alternative structure is employed for fixing the tensioned connectors to the sternal retractor (or another rigid support structure). For example, the connectors can be tied onto a rigid support or passed through a slot or tunnel and pinned in place.

The inventive clips exert sufficient gripping force on the pericardium to allow retraction of the heart (into a desired position) together as a unit with the pericardium and clips, and to maintain the heart in the desired position during surgery. In preferred embodiments in which the flexible connectors are elastic, the inventive apparatus does not rigidly constrain the heart muscle even when the heart is retracted, and the invention thus allows the retracted heart to retain its natural shape and performance even while it beats (e.g., while the surgery is performed on the beating heart while the beating heart is retracted by the inventive apparatus). Alternatively, since the pericardium has some compliance, non-elastic flexible connectors may be used during at least some types of beating heart surgery, since the freedom of the flexible connectors to twist and flex while bearing the load of the pericardium and retracted heart will prevent the inventive apparatus from rigidly constraining the heart muscle as it beats during such surgery on the retracted beating heart.

The foregoing is merely illustrative and explanatory of preferred embodiments of the inventive methods and apparatus. Various changes in the component sizes and shapes, and other details of the embodiments described herein may be within the scope of the appended claims.

What is claimed is:

1. An apparatus for retracting a heart by retracting an incised pericardium that partially surrounds the heart, including:

a support structure, wherein the support structure includes a fixed structure and a tined guide mounted to the fixed structure;

a clip; and a flexible connector having a first portion attached to the clip and a second portion releasably attached to the support structure such that the second portion of the flexible connector is fixed to the support structure when the clip is locked to the pericardium and the flexible connector exerts retracting force on the clip causing the pericardium to support the heart in a retracted position.

2. The apparatus of claim 1, wherein the fixed structure is a sternal retractor.

3. The apparatus of claim 2, wherein the tined guide includes a first portion mounted to the sternal retractor and a second portion defining a set of tines.

4. The apparatus of claim 1, wherein the tined guide includes a first portion mounted to the fixed structure and a second portion defining a set of tines, the flexible connector is a length of elastic tubing, and the second portion of the flexible connector is a segment of the elastic tubing squeezed between two of the tines.

5. The apparatus of claim 1, wherein said clip comprises a first element and a second element pivotally attached to the second element, wherein the first element defines a first jaw, the second element defines a second jaw, and the first element and the second element define a lock having a first configuration preventing the first jaw from pivoting away from the second jaw and a second configuration in which the first jaw is free to pivot away from the second jaw.

6. The apparatus of claim 5, wherein the flexible connector is an elastic flexible connector.

7. The apparatus of claim 5, further including:
   a second clip including a first element and a second element pivotably attached to the first element, wherein the first element defines a first jaw, the second element defines a second jaw, and the first element and the second element define a lock having a first configuration preventing the first jaw from pivoting away from the second jaw and a second configuration in which the first jaw is free to pivot away from the second jaw; and
   a second flexible connector having a first portion attached to the second clip and a second portion releasably attached to the support structure such that the second portion of the second flexible connector is fixed to the support structure when both the clip and the second clip are locked to the pericardium, and the flexible connector together with the second flexible connector support the pericardium and the heart in the retracted position.

8. The apparatus of claim 5, wherein the fist element of the clip defines a sawtooth rack, the second element of the clip defines a second sawtooth rack, and the sawtooth rack and the second sawtooth rack define the lock.

9. The apparatus of claim 8, wherein the first element of the clip and the second element of the clip are configured to be flexed relative to each other to disengage teeth of the sawtooth rack from teeth of the second sawtooth rack, thereby moving the clip from the first configuration to the second configuration.

10. The apparatus of claim 1, wherein the flexible connector is an elastic flexible connector.

11. The apparatus of claim 10, wherein the elastic flexible connector is a length of elastic tubing.

12. The apparatus of claim 1, wherein the flexible connector is a length of suture material.

13. The apparatus of claim 1, further including:
   a second clip including a first element and a second element pivotably attached to the first element, wherein the first element defines a first jaw, the second element defines a second jaw, and the first element and the second element define a lock having a first configuration preventing the first jaw from pivoting away from the second jaw and a second configuration in which the first jaw is free to pivot away from the second jaw; and
   a second flexible connector having a first portion attached to the second clip and a second portion releasably attached to the support structure such that the second portion of the second flexible connector is fixed to the support structure when both the clip and the second clip are locked to the pericardium, and the flexible connector together with the second flexible connector support the pericardium and the heart in the retracted position.

14. The apparatus of claim 1, further including:
   a second clip; and
   a second flexible connector having a first portion attached to the second clip and a second portion releasably attached to the support structure such that the second portion of the second flexible connector is fixed to the support structure when the second clip is locked to the pericardium and the second flexible connector exerts retracting force on the second clip;
   wherein the heart is a beating heart; and said clip, second clip, flexible connector and second flexible connector are configured to suspend the beating heart from the support structure in the retracted position, with the beating heart having the freedom to execute normal beating movement while suspended in the retracted position.

15. The apparatus of claim 1, further including:
   a second clip; and
   a second flexible connector having a first portion attached to the second clip and a second portion releasably attached to the support structure such that the second portion of the second flexible connector is fixed to the support structure when the second clip is locked to the pericardium and the second flexible connector exerts retracting force on the second clip;
   wherein the heart is a beating heart; and said clip and second clip are adapted to be locked on inferior incised edges of the pericardium near an apex of the heart, such that said clip, second clip, flexible connector and second flexible connector are configured to suspend the beating heart from the support structure in the retracted position, with the beating heart having the freedom to execute normal beating movement while suspended in the retracted position.

16. A method for using pericardial clips to retract a heart to a retracted position to facilitate surgery on the heart, wherein the clips are attached to flexible connectors with each of the clips attached to a different one of the flexible connectors, said method including the steps of:
   (a) incising a pericardium surrounding the heart to define incised edges of the pericardium;
   (b) after step (a), locking the clips to the incised edges of the pericardium; and
   (c) after step (b), tensioning the flexible connectors to cause the clips to lift the pericardium, thereby causing the pericardium to move the heart into the retracted position.

17. The method of claim 16, also including the step of:
   (d) after step (c), releasably fixing a portion of each of the flexible connectors to a support structure, thereby causing the pericardium to maintain the heart in the retracted position.

18. The method of claim 17, wherein the support structure includes a fixed structure and tined guides mounted to the fixed structure, and wherein step (d) includes the step of:
   fixing said portion of each of the flexible connectors to a different one of the tined guides.

19. The method of claim 17, wherein the fixed structure is a sternal retractor, each of the flexible connectors is a length of elastic tubing, and step (d) includes the step of squeezing said portion of each of the flexible connectors between tines of said different one of the tined guides.

20. The method of claim 17, wherein the flexible connectors are elastic connectors, the heart is a beating heart, and the elastic connectors have sufficient compliance to allow the pericardium to move during step (d) in a manner allowing the beating heart to execute normal beating movement during step (d).

21. The method of claim 16, wherein the heart has an apex, and step (b) includes the step of locking the clips to inferior incised edges of the pericardium near the apex of the heart.

22. The method of claim 16, wherein step (a) also includes the step of freeing the pericardium from adjacent pleura.

23. The method of claim 22, wherein the heart has an apex, and step (b) includes the step of locking the clips to inferior incised edges of the pericardium near the apex of the heart.

24. The method of claim 16, wherein each of the clips includes a first element and a second element pivotably attached to the second element, the first element defining a first jaw, the second element defining a second jaw, and the first element and the second element defining a lock having a first configuration preventing the first jaw from pivoting away from the second jaw and a second configuration in which the first jaw is free to pivot away from the second jaw, and wherein step (b) includes the step of:

locking the clips to the incised edges of the pericardium by placing each of the clips in its first configuration with the pericardium gripped between the first jaw and the second jaw of said each of the clips.

25. The method of claim 24, wherein the first element of each of the clips defines a sawtooth rack, the second element of each of the clips defines a second sawtooth rack, and the sawtooth rack and the second sawtooth rack define the lock of said each of the clips, and wherein step (b) includes the step of:

engaging teeth of the sawtooth rack with teeth of the second sawtooth rack, thereby moving the clip from the second configuration to the first configuration.

26. The method of claim 25, also including the steps of:

(d) after step (c), releasably fixing a portion of each of the flexible connectors to a support structure, thereby causing the pericardium to maintain the heart in the retracted position (e) after step (d), releasing said portion of each of the flexible connectors from the support structure, and flexing the first element of each of the clips relative to the second element of each of the clips to disengage the teeth of the sawtooth rack from teeth of the second sawtooth rack, thereby moving the clip from the first configuration to the second configuration.

27. The method of claim 16, wherein a first element of each of the clips defines a sawtooth rack, and a second element of each of the clips defines a second sawtooth rack, and the sawtooth rack and the second sawtooth rack define a lock of said each of the clips, and wherein step (b) includes the step of:

engaging teeth of the sawtooth rack with teeth of the second sawtooth rack, thereby moving the clip from a configuration in which the first jaw is free to pivot away from the second jaw to a configuration preventing the first jaw from pivoting away from the second jaw.

* * * * *